United States Patent [19]

McGraw

[11] 4,438,129

[45] Mar. 20, 1984

[54] USE OF CLOTRIMAZOLE TO TREAT HERPES LABIALIS

[75] Inventor: Isaac R. McGraw, Newtown, Pa.

[73] Assignee: Pennwalt Corporation, Philadelphia, Pa.

[21] Appl. No.: 424,121

[22] Filed: Sep. 27, 1982

[51] Int. Cl.³ .......................................... A61K 31/415
[52] U.S. Cl. ................................................ 424/273 R
[58] Field of Search .................................... 424/273 R

[56] References Cited

PUBLICATIONS

The Merck Index, 9th ed., 1976, Merck & Co. Inc., Rahway, N.J., pp. 309 and 310.

*Primary Examiner*—Jerome D. Goldberg

[57] ABSTRACT

Warm-blooded animals are treated for Herpes Simplex Virus-I by administering to the animal a dosage, effective to alleviate the symptoms of the virus, of Clotrimazole (chemically called 1-(o-chloro-α, α-diphenylbenzyl) imidazole) and at least one pharmaceutically acceptable carrier, wherein the compound is in the range of from about 0.01 to about 95% by weight of the composition.

2 Claims, No Drawings

USE OF CLOTRIMAZOLE TO TREAT HERPES LABIALIS

BACKGROUND OF THE INVENTION

This invention relates to a method of treating Herpes Simplex Virus-I (called herpes I) infections of the labial area in mammals and more particularly to a method of treating herpes I infections of the labial area in mammals with an antiviral composition containing Clotrimazole (chemically called 1-(o-chloro-α,α-diphenylbenzyl) imidazole), or its salts, and at least one pharmaceutically accepted carrier.

Herpes Labialis is an acute and recurring painful vesicular eruption of the oral mucosa in the vermilion borders of the lips. The causative agent is herpes virus, type I, and the initial infection usually occurs in childhood. Mild trauma such as sunburn, chapping, or fever may be a predisposing factor for a recurrent eruption; the common name for the lesion is a "cold sore".

The onset of a recurrent lesion is usually a feeling of fullness with a burning or itching sensation on the lips. This occurs before the typical vesicle develops. Vesicular lesions usually exist for several hours before the vesicle breaks or the fluid becomes secondarily infected. The lesions then become yellowish and crusted. The condition is self limiting, symptoms generally subsiding after from about 7 to 10 days.

No prior art is known which discloses the use of Clotrimazole for the treatment of herpes I.

SUMMARY OF THE INVENTION

This invention is directed to a method of treating herpes I infections of the labial area in mammals comprising administering to the mammal in need of said treatment an effective amount for treating the herpes I virus of a composition of Clotrimazole or its salts and at least one pharmaceutically acceptable carrier, wherein the compound is from about 0.01 to about 95% by weight of the composition.

DETAILED DESCRIPTION OF THE INVENTION

The Clotrimazole drug of this invention can be administered in the antiviral treatment according to this invention by any means that effects contact of the active ingredient compound with the site of virus infection in the body, after the infection sets in. The normal dosage form of the drug is topical application. The dosage form may be a solution, gel, emulsion, suspension, paste, ointment, powder, or other suitable formulation. The dosage of the drug administered will be dependent upon the virus being treated, i.e. herpes I, weight of the recipient, the frequency of treatment, and the effect desired. Generally in man, a daily topical dosage of active ingredient will be from about 5 milligrams to about 50 milligrams per application, although lower and higher amounts can be used. The active ingredient, the drug, can be employed in useful compositions according to the present invention in such dosage forms as solution, semisolid and solid form. These dosage forms preferrably deliver from about 5 milligrams to about 50 milligrams of active ingredient per application, with a range from about 10 milligrams to about 25 milligrams per application being preferred. In these dosage forms the antiviral composition will contain at least one non-toxic pharmaceutically acceptable carrier for the active ingredient.

Examples of the non-toxic carriers or adjuvants are viscosity enhancers such as bentonite, celluloses (e.g. methylcellulose, ethylcellulose, and carboxy methylcellulose), polyvinylpyrrolidone (PVP), tragacanth, glyceryl monostearate, cetyl alcohol, stearyl alcohol, synthetic spermaceti, and stearic acid; pH modifiers such as dibasic sodium phosphate, citric acid, and sodium hydroxide; preservatives such as methylparaben, propylparaben, benzoic acid, and benzyl alcohol; stability enhancers such as sodium bisulfite and ascorbic acid; coloring such as food, drug and cosmetic (FD&C) and drug and cosmetic (D&C) colors certified by the Food and Drug Administration (FDA); solvents such as water, alcohol (e.g. ethyl alcohol and isopropyl alcohol), polyethylene glycols, and propylene glycol; suspending agents such as kaolin, celluloses (e.g. methylcellulose, ethylcellulose, and carboxy methylcellulose), acacia and tragacanth; emulsifying agents such as glyceryl stearate, decyloleate, cetearyl alcohol, polysorbate 60 and triethanolamine; and humectants such as myristyl myristate.

Typical embodiments of the pharmaceutical composition of this invention are as follows: (all percentages are by weight of composition)

| Cream | |
|---|---|
| Clotrimazole | 0.05–10% |
| Sorbitan monostearate | 1–20% |
| Polysorbate 60 | 1–20% |
| Cetyl esters wax | 1–20% |
| Cetostearyl alcohol | 1–20% |
| 2-Octyl dodecanol | 0.1–10% |
| Benzyl alcohol | 0.1–5% |
| Water | 1–80% |
| Solution | |
| Clotrimazole | 0.05–20% |
| Polyethylene glycol 400 | 80–99.95% |

EXAMPLE

The Clotrimazole was tested for its antiviral activity against herpes I using a method that was developed by Sidwell.

The hair was shaved from both sides of female guinea pigs. These female guinea pigs were then innoculated with the herpes I virus for producing the lesions by spreading the virus over a measured area approximately 10 millimeter square ($mm^2$) and scratching within the area 10 times horizontally and 10 times vertically using an innoculating needle. The guinea pigs were then divided up into groups of five per group. 15 hours after innoculation with the virus, the drug treatment was begun; the drug was applied topically at the same dosage three times a day (TID) for six days. The drug was dissolved in a vanishing cream base at a concentration of 10 mg. of drug per milliliter of vehicle. Each animal was treated by applying the drug on the skin using three applications per lesion per treatment whereby each application delivered 0.15 grams of solution containing 1.5 milligrams of clotrimazole; therefore each dosage was approximately 4.5 milligrams. A placebo of the aqueous solution (control) dosage was used in the same manner as mentioned above on a second group of guinea pigs. The animals were observed each day for the six day period and the lesions, when visible, were measured and scored on the third day. In these experiments lesions were not observed until the second day after the drug treatment had begun. The third day of observation is when the measurement was made and also showed the effects of the drug treatment.

Calculations for antiviral activity of the drug are based on the average of the average lesion size for the third day for each group of animals. The difference between the control group and the test group is termed the reduction score which is a measure of the drug's antiviral activity and is expressed as percentage inhibition; the values are recorded in Table I.

The number of lesions recurring after the sixth day was also recorded in Table I.

TABLE I

|  | Day 3 | | Day 6 | |
| --- | --- | --- | --- | --- |
|  | Mean Lesion Size mm | % Inhibition | No. of New Lesions | % Inhibition |
| 1% Clotrimazole* | 18.9 | 17% | 13 | 80% |
| Vehicle Control | 22.8 | — | 66 | — |

*Clotrimazole is 1(o-chloro-α, α-diphenylbenzyl) imidazole

This data in Table I shows that on the third day when using a one percent (1%) Clotrimazole cream the lesions are reduced in treated animals. With the Clotrimazole treatment only thirteen of the lesions recurred but with the control treatment 66 lesions did recur.

What is claimed:

1. A method of treating herpes I infections of the labial area in mammals comprising topically administering to the mammal in need of said treatment an effective amount for treating the herpes I virus of a composition of 1(o-chloro-α,α-diphenylbenzyl) imidazole or its salts and at least one pharmaceutically acceptable carrier, wherein the compound is from about 0.01 to about 95% by weight of the composition.

2. The method of claim 1 wherein the 1(o-chloro-α,α-diphenylbenzyl) imidazole is dissolved at a 1% concentration in a homogeneous carrier of sorbitan monostearate, polyoxyethylene 20 sorbitan monostearate, cetyl esters wax, cetostearyl alcohol, 2-octyl dodecanol, benzyl alcohol, and water.

* * * * *